United States Patent [19]

Neumann

[11] 4,297,490
[45] Oct. 27, 1981

[54] BICYCLIC HETEROCYCLIC AMINO DERIVATIVES

[75] Inventor: Peter Neumann, Berne, Switzerland

[73] Assignee: Sandoz Ltd., Basel, Switzerland

[21] Appl. No.: 14,213

[22] Filed: Feb. 22, 1979

Related U.S. Application Data

[63] Continuation of Ser. No. 869,209, Jan. 13, 1978, abandoned.

[30] Foreign Application Priority Data

Jan. 14, 1977 [CH] Switzerland .................. 463/77

[51] Int. Cl.$^3$ .................. C07D 277/08; C07D 268/08
[52] U.S. Cl. .................. 544/55; 548/190; 548/193; 548/202; 548/134; 548/245; 424/270; 424/272
[58] Field of Search .................. 424/270, 272; 260/306.7 R, 207 R; 548/190, 193, 134, 202, 245; 544/54, 55

[56] References Cited

U.S. PATENT DOCUMENTS

| | | | |
|---|---|---|---|
| 2,992,232 | 7/1981 | Bloom | 260/330.5 |
| 3,499,083 | 3/1970 | Levitt | 424/246 |
| 3,808,335 | 4/1974 | Hess et al. | 424/246 |
| 3,843,668 | 10/1974 | Neuman | 260/304 |
| 3,847,934 | 11/1974 | Neumann et al. | 260/309.6 |
| 4,159,335 | 6/1979 | Neustadt | 424/270 |

FOREIGN PATENT DOCUMENTS 2040374 2/1971 Fed. Rep. of Germany .
2257311 6/1973 Fed. Rep. of Germany .

Primary Examiner—Nicholas S. Rizzo
Attorney, Agent, or Firm—Gerald D. Sharkin; Richard E. Vila; Joseph J. Borovian

[57] ABSTRACT

The present invention concerns compounds of formula

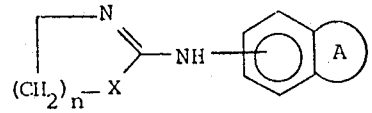

wherein X is O, S or NH; n is 1 or 2 and A is a 5-membered heterocyclic ring, wherein the bicyclic system may be substituted.

The compounds are useful as myotonolytic and antihypertensive agents.

24 Claims, No Drawings

BICYCLIC HETEROCYCLIC AMINO DERIVATIVES

This is a continuation, of application Ser. No. 869,209 filed Jan. 13, 1978, now abandoned.

This invention relates to bicyclic heterocyclic derivatives.

The present invention concerns compounds of formula I,

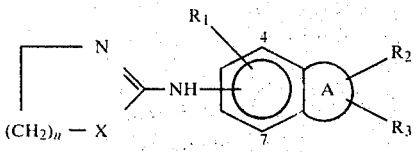

wherein
x is oxygen, sulphur or imino,
n is 1 or 2,
$R_1$ is hydrogen, halogen, alkyl($C_{1-4}$), alkylthio($C_{1-4}$), alkoxy($C_{1-4}$), trifluoromethyl or hydroxy,
A is a five-membered heterocyclic ring containing at least one heteroatom chosen from nitrogen, oxygen and sulphur and having 2 adjacent carbon atoms common with the benzene ring, with the proviso that the bicyclic moiety comprising A and the benzene ring is other than 2,1,3-benzothiadiazole and indazole, and
$R_2$ and $R_3$ are substituents which may be present in ring A, wherein
$R_2$ is attached to a ring carbon atom and is hydrogen, halogen, alkyl($C_{1-4}$), alkoxy($C_{1-4}$), alkylthio($C_{1-4}$), trifluoromethyl or hydroxy and
$R_3$ is attached to a ring nitrogen atom and is hydrogen or alkyl($C_{1-4}$), with the proviso that
  (i) when A is [c]pyrrole, the nitrogen atom of A is substituted by alkyl($C_{1-4}$),
  (ii) when A is [b]thiophen or [b]furan, X is oxygen and n is 1, the oxazolinylamino side chain is attached to position 4 or 7 of the bicyclic moiety, and
  (iii) when A is [b]thiophene, X is imino and n is 1, the imidazolinylamino side chain is attached to 45 position 4 or 7 of the bicyclic moiety.

It has been found that these compounds exhibit monotonolytic activity in standard tests in animals, e.g. as described hereinafter.

Compounds of formula I other than the compounds:
(1) 4-(2-imidazolin-2-yl)amino-5-chlorobenzo[b]thiophene,
(2) 4-(2-imidazolin-2-yl)amino-5-bromobenzo[b]thiophene,
(3) 4-(2-imidazolin-2-yl)amino-3,5-dichlorobenzo[b]thiophene,
(4) 4-(2-imidazolin-2-yl)amino-3,5-dibromobenzo[b]thiophene,
(5) 7-(2-imidazolin-2-yl)amino-6-chlorobenzo[b]thiophene,
(6) 7-(2-imidazolin-2-yl)amino-6-bromobenzo[b]thiophene,
(7) 4-(2-imidazolin-2-yl)amino-3-bromobenzo[b]thiophene, and
(8) 4-(2-imidazolin-2-yl)amino-benzo[b]thiophene
are new and are hereinafter referred to as compounds of formula I'. Compounds (1) to (6) are known and stated to be active as vasoconstrictors and anti-hypertensives.

Compounds (7) and (8) are known but are not stated to be active as pharmaceuticals.

The compounds of formula I may exist in tautomeric forms, e.g. in the tautomeric form of formula Ia,

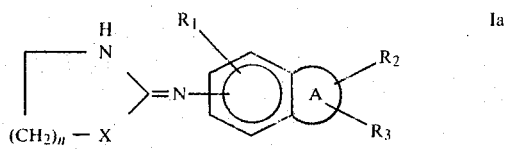

When $R_2$ is hydroxy, the corresponding keto form may also exist. All such tautomeric forms are encompassed in the present compounds of formula I.

A may have one or two double bonds. One double bond may be common with the benzene ring. If two double bonds are present, each of these may be exocyclic to the benzene ring. A contains preferably 3, 2 or 1 nitrogen atom and/or one oxygen atom or sulphur atom.

A is, for example, [b] or [c]pyrrole, [d]imidazole, [d]triazole, [b] or [c]furan, [c] or [d]isoxazole, [d]oxazole, [c]furazan, [b] or [c]thiophene, [c] or [d]isothiazole, [d]thiazole, [d](1,2,3)-thiadiazole, [b] or [c]pyrroline, [b] or [c]dihydrofuran or [b]dihydrothiophene. Preferably A is [b]furan, [b]thiophene, [d]oxazole or [d]triazole, especially [b]furan.

Halogen means fluorine, chlorine, bromine or iodine, preferably bromine or chlorine.

Alkyl, alkoxy or alkylthio preferably contains 2 carbon atoms, especially 1 carbon atom. $R_1$ is preferably other than hydroxy and is preferably hydrogen, chlorine or methyl. $R_1$ is preferably ortho to the heterocyclic-amino moiety. $R_2$ is preferably alkyl, hydrogen or halogen, especially chlorine. The heterocyclic-amino residue is preferably attached to position 4 or 7 of the bicyclic moiety. When the heterocyclic-amino moiety is attached to the 4 position of the bicyclic moiety, than $R_2$, when present, is preferably in the 3 position. $R_3$, when present, is preferably alkyl. n is preferably 1.

The present invention also provides a process for the production of a compound of formula I', as defined above, which comprises, (a) for the production of a compound of formula I', wherein X is oxygen or sulphur, cyclising a compound of formula II,

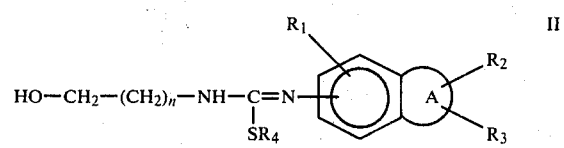

wherein A, $R_1$, $R_2$, $R_3$ and n are as defined above, and $R_4$ is hydrogen or alkyl($C_{1-4}$) or a tautomeric form thereof when $R_4$ is hydrogen, with the proviso that when X in the resultant compound of formula I' is sulphur, then $R_4$ is hydrogen, or (b) for the production of a compound of formula I' wherein X is imino, reacting a compound of formula III,

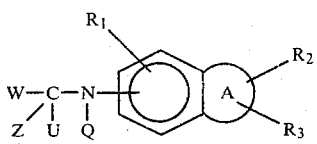

wherein $R_1$, $R_2$, $R_3$ and A are as defined above, and either (i) Q is hydrogen and W, Z and U together with the carbon atoms to which they are bound are cyano, or (ii) Q and W together form a single bond and Z and U are, independently, leaving groups, with a compound of formula IV, $$H_2N.CH_2.(CH_2)_n.NH_2 \qquad IV$$

wherein n is as defined above.

Process (a) may be effected in conventional manner for the production of analogous compounds. The production of a compound of formula I' wherein X is oxygen is conveniently effected in the presence of a base, e.g. in alkali metal hydroxide or alkaline earth metal hydroxide, e.g. potassium or sodium hydroxide, or an alkali metal alcoholate, e.g. sodium or potassium methylate, and/or in the presence of mercury acetate or lead acetate. The production of a compound of formula I' wherein X is sulphur is conveniently effected in the presence of an acid, e.g. hydrochloric acid, sulphuric acid or methanesulphonic acid.

Process (b) may be effected in conventional manner for the production of analogous compounds. In formula II, U and Z may be the same or different and may be, for example, $R_5S-$, $R_5NH-$, $R_5O$ or $O_2NNH-$, wherein $R_5$ is hydrogen or alkyl of 1 to 3 carbon atoms, or each may be chlorine. Preferably U is $SCH_3$ and Z is $NH_2$.

The compounds of formula II wherein $R_4$ is hydrogen may be made by reacting the corresponding bicyclic amine with thiophosgene to give the corresponding isothiocyanate, which is then reacted with ethanolamine or propanolamine. The compounds of formula II wherein $R_4$ is alkyl may be made by alkylating the corresponding compounds of formula II wherein $R_4$ is hydrogen.

The starting materials are known or may be made in conventional manner.

Free base forms of the compounds of formula I may be converted into acid addition salt forms in conventional manner and vice versa. Suitable acids for salt formation include acetic acid, maleic acid and hydrochloric acid.

In the following Examples, all temperatures are in degrees Centigrade and are uncorrected.

In the Tables, the positions of $R_1$, $R_2$ or $R_3$ refer to the position on the bicyclic moiety and y is the position of the heterocyclic-amino moiety in the bicyclic moiety. When the position of $R_2$ or $R_3$, when hydrogen, is not given, e.g. for A=imidazole, then $R_2$ or $R_3$ is attached to any appropriate carbon or nitrogen atom respectively of A.

EXAMPLE 1

7-(2-Oxazolin-2-yl)amino-benzo[b]furan

[Process (a)]

5.4 g of N-benzo[b]furan-7-yl-N'-2-hydroxyethylthiourea in 300 ml of ethanol are boiled under reflux and are treated with a solution of 1.12 g of sodium in 25 ml of ethanol. The hot mixture is treated with 8.1 g of mercury(II) acetate over ½ minute, refluxed for 15 minutes and then filtered. The filtrate is evaporated to dryness. The residue is partitioned between 40 ml of 1 N hydrochloric acid and 40 ml of methylene chloride. The aqueous phase is treated with active charcoal, filtered and made alkaline with concentrated ammonia solution. The resultant precipitate is filtered, dried and recrystallised from ethyl acetate to give the title compound in free base form. M.Pt. 124°–6°.

The starting material is obtained as follows:

7-Amino-benzo[b]furan is reacted with thiophosgene in 3 N hydrochloric acid at room temperature over 1 hour to give 7-isothiocyanatobenzo[b]furan. (M.Pt. 45°–46° from petroleum ether.) Reaction of this isothiocyanate with ethanolamine in ether gives N-benzo[b]furan-7-yl-N'-2-hydroxyethylthiourea (m.pt. 138°–139° from methanol) which is used further in the crude state.

EXAMPLE 2

In analogous manner to that described in Example 1, the following compounds of formula I are obtained when X is oxygen:

| Ex. No. | A | n | y | $R_1$ | $R_2$ | $R_3$ | M.Pt. |
|---|---|---|---|---|---|---|---|
| (a) | [b]Dihydrofuran | 1 | 5 | H | H | — | 158–160° |
| (b) | [b]Thiophene | 1 | 7 | H | 3-$CH_3$ | — | 157–161° |
| (c) | [d]Triazole | 1 | 4 | 5-Cl | — | 2-$CH_3$ | 178–185° |
| (d) | [d]Triazole | 1 | 7 | H | — | 1-$CH_3$ | 175–178° |
| (e) | [b]Pyrrole | 1 | 7 | H | H | 1-$CH_3$ | |
| (f) | [b]Pyrrole | 1 | 4 | H | H | 1-$CH_3$ | |
| (g) | [b]Furan | 1 | 4 | H | H | — | |
| (h) | [b]Thiophene | 1 | 4 | H | H | — | |
| (i) | [d]Oxazole | 1 | 7 | H | H | — | |
| (j) | [d]Imidazole | 1 | 7 | H | H | 1-$CH_3$ | 135–137° |

EXAMPLE 3

7-(2-Thiazolin-2-yl)amino-benzo[b]furan

[Process (a)]

3 g of N-benzo[b]furan-7-yl-N'-2-hydroxyethylthiourea in 12 ml of concentrated hydrochloric acid are heated for 10 minutes on a steam bath. The mixture is treated with 60 ml of water, treated with active charcoal and filtered. The colourless filtrate is made basic with conc. aqueous medium hydroxide solution. The resultant precipitate is filtered off. After recrystallisation from methanol/ether, the title compound is obtained in free base form. M.Pt. 143°–145°.

EXAMPLE 4

In analogous manner to Example 3 and using corresponding starting materials, the following compounds of formula I wherein X is sulphur are obtained:

| Ex. No. | A | n | y | $R_1$ | $R_2$ | $R_3$ | M.Pt. |
|---|---|---|---|---|---|---|---|
| (a) | [b]Furan | 1 | 5 | H | H | — | 122–123° |
| (b) | [b]Dihydrofuran | 2 | 5 | H | H | — | 148–149.5° |
| (c) | [b]Furan | 2 | 5 | H | H | — | 145–146° |
| (d) | [d]Triazole | 1 | 4 | 5-Cl | — | 2-$CH_3$ | 186–194° |
| (e) | [d]Triazole | 1 | 7 | H | — | 1-$CH_3$ | 167.5–169.5° |

EXAMPLE 5

4-(2-Imidazolin-2-yl)amino-5-methyl-2,1,3-benzoxadiazole [Process (b)] [A=[c]furazan]

16.4 g of S-methyl-N-(5-methyl-2,1,3-benzoxadiazol-4-yl) isothiouronium iodide are suspended in 100 ml of methanol, and the suspension treated with 3.5 ml of ethylene diamine. The mixture is boiled under reflux for 1 hour. The solvent is evaporated off and the residue heated for 2 hours at 140°. The cooled product is partitioned between 200 ml of chloroform and 50 ml of 2 N aqueous sodium hydroxide solution. The organic phase is dried and evaporated. The residue affords after recrystallisation from methanol 4-(2-imidazolin-2-yl)-5-methyl-2,1,3-benzoxadiazole. M.pt. 219°–221°.

The starting material is obtained as follows:

A solution of 12 g of ammonium rhodanide in 300 ml acetone cooled with an ice bath is treated with 14 ml of benzoyl chloride and stirred for 10 minutes. This solution is boiled together with 15.5 g of 4-amino-5-methyl-2,1,3-benzoxadiaxole under reflux for 1 hour, cooled and then diluted with a 4-fold quantity of water. The resultant precipitate is filtered off and mixed together with 200 ml of 2 N aqueous sodium hydroxide. The mixture is quickly brought to boiling. After 5 minutes, the solution is cooled and made acid with glacial acetic acid. The resultant precipitate is filtered off and washed with water, and a little boiling methanol, and then with ether. The resultant N-(5-methyl-2,1,3-benzoxadiazol-4-yl) thiourea in 160 ml of methanol with 14 g of methyl iodide is heated for 1 hour and then evaporated to dryness to give crude S-methyl-N-(5-methyl-2,1,3-benzoxadiazol-4-yl) isothiouronium iodide which is used in the crude state.

EXAMPLE 6

In analogous manner to Example 5, the following compounds of formula I may be produced wherein X is imino:

| Ex. No. | A | n | y | $R_1$ | $R_2$ | $R_3$ | M.Pt. |
|---|---|---|---|---|---|---|---|
| (a) | [b]Dihydrofuran | 1 | 5 | H | H | — | 168–170° |
| (b) | [d]Triazole | 1 | 4 | H | — | H | 283–287° |
| (c) | [d]Triazole | 1 | 4 | 5-CH$_3$ | — | H | 281–285° |
| (d) | [d]Triazole | 1 | 4 | 5-Cl | — | H | 259–263° |
| (e) | [d]Triazole | 1 | 4 | H | — | 1-CH$_3$ | 181–182° |
| (f) | [d]Triazole | 1 | 4 | 5-OCH$_3$ | — | 1-CH$_3$ | 201–204° |
| (g) | [d]Triazole | 1 | 4 | 5-Cl | — | 1-CH$_3$ | 216–218° |
| (h) | [d]Triazole | 1 | 7 | H | — | 1-CH$_3$ | 219–222° |
| (i) | [d]Triazole | 1 | 4 | H | — | 2-CH$_3$ | 200–202° |
| (j) | [d]Triazole | 1 | 4 | 5-OCH$_3$ | — | 2-CH$_3$ | 245–251° |
| (k) | [d]Triazole | 1 | 4 | 5-Cl | — | 2-CH$_3$ | 236–242° |
| (l) | [d]Triazole | 2 | 7 | H | — | 1-CH$_3$ | 252–254° |
| (m) | [d]Triazole | 2 | 4 | H | — | 2-CH$_3$ | 223–227° |
| (n) | [d]Imidazole | 1 | 4 | H | H | H | 265–268° |
| (o) | [d]Imidazole | 1 | 7 | H | H | 1-CH$_3$ | 269–272° |
| (p) | [b]Pyrrole | 1 | 4 | H | H | H | 222–224° |
| (q) | [b]Pyrrole | 1 | 7 | H | H | H | 223–225° |
| (r) | [b]Pyrrole | 1 | 7 | H | H | 1-CH$_3$ | 139–142° |
| (s) | [d]1,2,3-Thiadiazole | 1 | 7 | 6-Cl | — | — | 281–283° |
| (t) | [c]Furazan | 1 | 4 | H | — | — | 164–166° |
| (u) | [c]Furazan | 1 | 4 | 5-OCH$_3$ | — | — | 212–215° |
| (v) | [c]Furazan | 1 | 4 | 5-Cl | — | — | 239–241° |
| (w) | [c]Furazan | 1 | 5 | H | — | — | 226–228° |
| (x) | [c]Furazan | 1 | 4 | 7-Cl | — | — | 258–260° |
| (y) | [c]Furazan | 1 | 5 | 4-Br | — | — | 256–260° (decomp.) |
| (z) | [b]Furan | 1 | 7 | H | H | — | |
| (aa) | [d]Imidazole | 1 | 7 | H | 2-CH$_3$ | 1-CH$_3$ | 310–315° |
| (ab) | [b]Pyrrole | 2 | 5 | 4-SC$_2$H$_5$ | 2-Cl | 1-C$_2$H$_5$ | |
| (ac) | [c]Pyrrole | 2 | 5 | 7-CF$_3$ | 3-SC$_2$H$_5$ | 2-C$_2$H$_5$ | |
| (ad) | [c]Isoxazole | 2 | 5 | 4-OH | H | — | |
| (ae) | [d]Isoxazole | 2 | 5 | 7-OC$_2$H$_5$ | H | — | |
| (af) | [c]Isothiazole | 2 | 5 | 7-OC$_2$H$_5$ | H | — | |
| (ag) | [d]Isothiazole | 2 | 5 | 7-OC$_2$H$_5$ | H | — | |
| (ah) | [d]Thiazole | 2 | 5 | 7-OC$_2$H$_5$ | H | — | |
| (ai) | [c]Thiophene | 2 | 5 | 7-OC$_2$H$_5$ | H | — | |
| (aj) | [b]Pyrroline | 2 | 5 | 7-OC$_2$H$_5$ | 3-OC$_2$H$_5$ | 1-H | |
| (ak) | [c]Pyrroline | 2 | 5 | 7-OC$_2$H$_5$ | H | 2-H | |
| (al) | [c]Furan | 2 | 5 | 7-OC$_2$H$_5$ | 3-CF$_3$ | — | |
| (am) | [c]Dihydrofuran | 2 | 5 | 7-OC$_2$H$_5$ | H | — | |
| (an) | [b]Dihydrothiophene | 2 | 5 | 7-OC$_2$H$_5$ | 3-OH | — | |

The compounds of formula I are useful as myotonolytics, for example, for the treatment of spastic conditions of different etiology (neurological, inflammatory, rheumatic, etc.) and as muscle relaxants, as indicated by standard tests. For example, in rabbits on i.v. administration of from 0.001 to 10 mg/kg animal body weight of the compounds a significant muscle relaxing effect is observed in accordance with the method of Teschendorf et al.. Arch. Exp. Pharmacol. 266, 467–468 (1970).

The compounds of formula I wherein A is [b]-thiophene or [b]furan, X is oxygen and n is 1 exhibit more beneficial activity than expected for such compounds. The preferred compound is the Example 1 compound.

For the above-mentioned novel uses, the dosage will, of course, vary depending on the compound employed, mode of administration and therapy desired. However, in general, satisfactory results are obtained with a daily dosage of from 0.0001 to about 10 mg/kg animal body weight, conveniently given in divided doses 2 to 4 times a day or in sustained release form. For the larger mammal, the total daily dosage is in the range from about 0.01 to about 10 mg, e.g. between 1 and 6 mg, preferably between 1.5 and 3 mg.

A pharmaceutical composition in unit dosage form may contain from about 0.002 to about 5 mg (e.g. from 0.025 to 5 mg) of a compound of formula I in association with a solid or liquid pharmaceutical carrier or diluent.

The compounds of formula I' additionally are useful as anti-hypertensive agents, as indicated by a blood pressure lowering activity in standard tests. For example, the compounds exhibit a blood pressure lowering effect in the Grollmann rat tests [see A. Grollmann, Proc. Soc. Expt. Biol. and Med. 57, 104 (1944)] on s.c. administration of from 0.1 to 10 mg/kg animal body weight of the compounds, and in the Goldblatt dog test on s.c. administration of from 0.1 to 10 mg/kg animal body weight of the compounds.

For this use, the dosage will, of course, vary depending on the compound employed, mode of administration and treatment desired. However, in general, satisfactory results are obtained when administered at a daily dosage of from about 0.1 to about 10 mg/kg animal body weight, conveniently given in divided doses 2 to 4 times a day or in sustained release form. For the larger mammals, the total daily dosage is in the range from about 10 to about 200 mg, and dosage forms suitable for oral administration comprise from about 2 mg to about 100 mg of the compounds admixed with a solid or liquid pharmaceutical carrier or diluent.

The Example 1 compound is the preferred compound and has been found to be an effective anti-hypertensive agent in hypertensive dogs at a daily dose of 0.1 mg/kg. s.c.

The myotonolytic use is the preferred use of the compounds.

The compounds of formula I may be administered in pharmaceutically acceptable acid addition salt form, e.g. the hydrochloride or maleate. Such acid addition salt forms exhibit the same order of activity as the free base forms and are readily prepared in conventional manner. The present invention also provides a pharmaceutical composition comprising a compound of formula I', or 4-(2-imidazolin-2-yl)amino-3-bromobenzo[b]thiophene or 4-(2-imidazolin-2-yl)amino-benzo[b]thiophene, in free base form or in pharmaceutically acceptable acid addition salt form, in association with a pharmaceutical carrier or diluent. Such compositions may be in the form of, for example, a solution or a tablet.

The compositions may already be in the final form ready for administration, for example in the form of integral solid dosage forms, e.g. a tablet. The composition may be packaged to facilitate administration of a unit dosage form, e.g. an ampoule containing a sterile injectable liquid.

The compositions may be in bulk form, e.g. when the form of a liquid, a powder, or granules. Such forms may contain the compound of formula I in such a concentration that a conveniently administered portion recognised in the art, e.g. from 1 to 10 ml, e.g. a teaspoonful, contains the required dosage of compound of formula I.

As indicated above the compounds may be administered orally in the form of tablets, powders, granules, capsules, suspensions, sirups and elixirs, or parenterally in the form of injectable solutions or suspensions. Aside from the compound of formula I the compositions may contain pharmaceutically inert organic or inorganic adjuvants, optionally granulating agents, binding agents, lubricants, dispersing agents, wetting agents and preservatives. Moreover, the pharmaceutical compositions may contain colouring, flavouring and sweeting substances, etc. Adjuvants for the production of tablets may be calcium carbonate, lactose, microcrystalline cellulose, mannitol, or talc. Starch and alginic acid or microcrystalline cellulose may be used as granulating and disintegrating agents, starch, polyvinylpyrrolidone and gelatine may be used as binding agents, and magnesium stearate, stearic acid, colloidal silicon dioxide and talc as lubricants. Tablet formulations may be coated or uncoated, with the coating being applied in a manner per se and having the purpose of delaying the disintegration and adsorption in the gastrointestinal tract, thus providing a retarded effect over a longer period. Suitable suspending agents for the production of liquid administration forms are especially methyl cellulose, tragacanth and sodium alginate. Suitable wetting agents are e.g. polyoxyethylene stearate and polyoxyethylene sorbitan-monooleate. Furthermore, preservatives such as p-hydroxy-benzoic acid alkyl ester may be used. Capsule formulations may contain the compound of formula I on its own or together with an inert solid diluent, for example calcium phosphate, starch, lactose, mannitol, colloidal silicon dioxide and microcrystalline cellulose.

Solid preparations are preferred, especially hard-filled capsules and tablets, for reasons of easier production and favourable administration.

Tablets and capsules containing the following constituents may be made in conventional manner:

| Component | Weight (mg) Tablet | Weight (mg) Capsule |
| --- | --- | --- |
| 4-(2-Imidazolin-2-yl)amino-benzo-[b]thiophene or the 3-bromo derivative thereof (active agent) | 0.5 | 2.0 |
| Lactose | 70.5 | 173.5 |
| Microcrystalline cellulose | 18.0 | — |
| Corn starch | — | 120.0 |
| Colloidal silicic acid | 0.5 | 1.5 |
| Magnesium stearate | 0.5 | 3.0 |
| | 90.0 | 300.0 |

These tablets and capsules may be used for the treatment of spastic conditions at a dose of 1 to 2 tablets 4 times daily or 2 capsules 2 to 4 times daily.

If desired, the active agent may be replaced by an equivalent amount of any one of the compounds (1) to (6) listed above after formula I above, or any other compound of formula I.

The following scopes of the compounds are envisaged:
1. A compound of formula I wherein A is [b]pyrrole.
2. A compound of formula I wherein A is [c]pyrrole.
3. A compound of formula I wherein A is [d]imidazole.
4. A compound of formula I wherein A is [d]triazole.
5. A compound of formula I wherein A is [b]furan.
6. A compound of formula I wherein A is [c]furan.
7. A compound of formula I wherein A is [c]isoxazole.
8. A compound of formula I wherein A is [d]isoxazole.
9. A compound of formula I wherein A is [d]thiazole.
10. A compound of formula I wherein A is [d]1,2,3-thiadiazole.

11. A compound of formula I wherein A is [b]pyrroline.
12. A compound of formula I wherein A is [c]pyrroline.
13. A compound of formula I wherein A is [b]dihydrofuran.
14. A compound of formula I wherein A is [c]dihydrofuran.
15. A compound of formula I wherein A is [b]dihydrothiophene.
16. A compound of formula I wherein A is [d]oxazole.
17. A compound of formula I wherein A is [c]furazan.
18. A compound of formula I wherein A is [b]thiophene.
19. A compound of formula I wherein A is [c]thiophene.
20. A compound of formula I wherein, when A is thiophene, $R_2$ and $R_3$ are other than halogen.
21. A compound of formula I wherein A is other than thiophene.
22. A compound of formula I wherein $R_2$ is hydrogen, A is [b]dihydrofuran or [b]furan, and the heterocyclicamino moiety is in the 5 or 7 position of the bicyclic moiety.

What is claimed is:
1. A compound having the formula

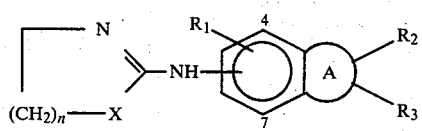

wherein
X is oxygen or sulfur, the heterocyclic amino moiety is bonded to the benzene ring of the bicyclic moiety,
n is an integer 1 or 2,
$R_1$, which is bonded to the benzene ring of the bicyclic moiety, is hydrogen, halo, $C_{1-4}$alkyl, $C_{1-4}$alkylthio, $C_{1-4}$alkoxy, trifluoromethyl or hydroxy,
A is a five-membered heterocyclic ring selected from the group consisting of [b]pyrrole, [c]pyrrole, [d]triazole, [b]furan, [c]furan, [c]furazan, [d](1,2,3)-thiadiazole, [b]pyrroline, [c]pyrroline, [b]dihydrofuran, [c]dihydrofuran, [b]dihydrothiophene, [c]isoxazole and [d]isoxazole,
$R_2$, which is bonded to the A ring of the bicyclic moiety and attached to a carbon atom of said ring, is hydrogen, halo, $C_{1-4}$alkyl, $C_{1-4}$alkoxy, $C_{1-4}$alkylthio, trifluoromethyl or hydroxy, and
$R_3$, which is bonded to the A ring of the bicyclic moiety and attached to a nitrogen atom of said ring, is hydrogen or $C_{1-4}$alkyl, with the provisos that:
(i) when A is [c]pyrrole, the nitrogen atom is $C_{1-4}$alkyl-substituted, and
(ii) when A is [b]furan, X is oxygen and n is 1, the oxazolinylamino group is attached to either the 4- or 7-position of the bicyclic moiety,
said compound being in free base or in pharmaceutically acceptable acid addition salt form.
2. A compound according to claim 1 wherein A is [b]pyrrole, said compound being in free base or in pharmaceutically acceptable acid addition salt form.
3. A compound according to claim 2 wherein the heterocyclic amino moiety is bonded to the 4- or 7-position of the bicyclic moiety, said compound being in free base or in pharmaceutically acceptable acid addition salt form.
4. The compound according to claim 3 which is 1-methyl-7-(2-oxazolin-2-yl)amino-benzo[b]pyrrole.
5. The compound according to claim 3 which is 1-methyl-4-(2-oxazolin-2-yl)amino-benzo[b]pyrrole.
6. A compound according to claim 1 wherein A is [d]triazole, said compound being in free base or in pharmaceutically acceptable acid addition salt form.
7. A compound according to claim 6 wherein the heterocyclic amino moiety is bonded to the 4- or 7-position of the bicyclic moiety, said compound being in free base or in pharmaceutically acceptable acid addition salt form.
8. The compound according to claim 7 which is 5-chloro-2-methyl-4-(2-oxazolin-2-yl)amino-benzo[d]triazole.
9. The compound according to claim 7 which is 1-methyl-7-(2-oxazolin-2-yl)amino-benzo[d]triazole.
10. The compound according to claim 7 which is 5-chloro-2-methyl-4-(2-thiazolin-2-yl)amino-benzo[d]triazole.
11. The compound according to claim 7 which is 1-methyl-7-(2-thiazolin-2-yl)amino-benzo[d]triazole.
12. A compound according to claim 1 wherein A is [b]furan, said compound being in free base or in pharmaceutically acceptable acid addition salt form.
13. A compound according to claim 12 wherein the heterocyclic amino moiety is bonded to the 4- or 7-position of the bicyclic moiety, said compound being in free base or in pharmaceutically acceptable acid addition salt form.
14. The compound according to claim 13 which is 7-(2-oxazolin-2-yl)amino-benzo[b]furan.
15. The compound according to claim 13 which is 4-(2-oxazolin-2-yl)amino-benzo-[b]furan.
16. The compound according to claim 13 which is 7-(2-thiazolin-2-yl)amino-benzo[b]furan.
17. The compound according to claim 12 which is 5-(2-thiazolin-2-yl)amino-benzo[b]furan.
18. The compound according to claim 12 which is 5-(5,6-dihydro-4H-1,3-thiazin-2-yl)amino-benzo[b]furan.
19. A compound having the formula

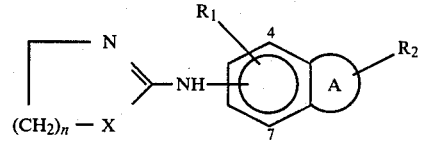

wherein
X is oxygen or sulfur, the heterocyclic amino moiety is bonded to the benzene ring of the bicyclic moiety,
n is an integer 1 or 2,
$R_1$, which is bonded to the benzene ring of the bicyclic moiety, is hydrogen, halo, $C_{1-4}$ alkyl, $C_{1-4}$alkylthio, $C_{1-4}$alkoxy, trifluoromethyl or hydroxy,
A is [b]thiophene or [c]thiophene, and
$R_2$ which is bonded to the A ring of the bicyclic moiety and attached to a carbon atom of said ring, is hydrogen, halo, $C_{1-4}$alkyl, $C_{1-4}$alkoxy, $C_{1-4}$alkylthio, trifluoromethyl or hydroxy, with the proviso that when A is [b]thiophene, X is oxygen and n is 1, the oxazolinylamino group is attached to either the 4- or 7-position of the bicyclic moiety, said compound being in free base or in pharmaceutically acceptable acid addition salt form.

20. A compound according to claim 19 wherein the heterocyclic amino moiety is bonded to the 4- or 7-position of the bicyclic moiety, said compound being in free base or in pharmaceutically acceptable acid addition salt form.

21. A compound acccording to claim 20 which is 3-methyl-7-(2-oxazolin-2-yl)amino-benzo[b]thiophene.

22. A compound according to claim 20 which is 4-(2-oxazolin-2-yl)amino-benzo[b]thiophene.

23. A compound according to claim 1 wherein A is [d](1,2,3)-thiadiazole, said compound being in free base or in pharmaceutically acceptable acid addition salt form.

24. A compound according to claim 1 wherein A is [c]furazan, said compound being in free base or in pharmaceutically acceptable acid addition salt form.

* * * * *

UNITED STATES PATENT AND TRADEMARK OFFICE
CERTIFICATE OF CORRECTION

PATENT NO. : 4,297,490

DATED : October 27, 1981

INVENTOR(S) : Peter Neumann

It is certified that error appears in the above—identified patent and that said Letters Patent is hereby corrected as shown below:

Column 4, line 50; after "aqueous", change "medium" to -- sodium --.

Signed and Sealed this

Nineteenth Day of April 1983

[SEAL]

Attest:

Attesting Officer

GERALD J. MOSSINGHOFF

Commissioner of Patents and Trademarks